United States Patent [19]

Ohnishi et al.

[11] Patent Number: 5,270,552

[45] Date of Patent: Dec. 14, 1993

[54] METHOD FOR SEPARATING SPECIMEN AND METHOD FOR ANALYZING THE SPECIMEN SEPARATED BY THE SPECIMEN SEPARATING METHOD

[75] Inventors: Tsuyoshi Ohnishi; Tohru Ishitani, both of Katsuta, Japan

[73] Assignee: Hitachi, Ltd., Tokyo, Japan

[21] Appl. No.: 933,232

[22] Filed: Aug. 21, 1992

[30] Foreign Application Priority Data

Aug. 22, 1991 [JP] Japan .................. 3-210803

[51] Int. Cl.$^5$ ........................................ H01J 37/305
[52] U.S. Cl. .................. 250/307; 250/492.21; 250/309
[58] Field of Search .................... 250/307, 309, 492.21, 250/398

[56] References Cited

U.S. PATENT DOCUMENTS

| 4,939,364 | 7/1990 | Ishitani et al. | 250/309 |
| 5,086,230 | 2/1992 | Adachi et al. | 250/309 |
| 5,093,572 | 3/1992 | Hosmo | 250/309 |
| 5,149,973 | 9/1992 | Morimoto | 250/492.21 |

OTHER PUBLICATIONS

"Cross-sectional transmission electron microscopy of precisely selected regions from semiconductor devices", Kirk et al. *Inst. Phys. Conference* No. 100: Section 7, Apr. 1989, pp. 501-506.

"New Applications of Focused ion Beam Tech. to Failure Analysis and Process monitoring of VLSI", Nikawa et al., Proceedings of Internation Reliability Physics Symposium, 1989, pp. 43-52.

*Primary Examiner*—Bruce C. Anderson
*Attorney, Agent, or Firm*—Antonelli, Terry, Stout & Kraus

[57] ABSTRACT

When a desired portion is separated from an integrated circuit chip or a semiconductor wafer, the portion is separated without dividing the chip or the wafer, so that the separated specimen can be moved to a desired position, and the separated specimen can be set to a desired attitude. Therefore, various analyses on the specimen through TEM, SEM, SIMS and so on can be carried out. A minute piece of specimen is cut and separated from the substrate of a specimen by use of a three-dimensional minute processing technique and a micromanipulation technique. A surface of the specimen is subjected to an FIB processing from at least two kinds of angles, the separated specimen being mechanically connected to an external probe in a step for separating a part of the specimen including a portion to be analyzed. The separated specimen is supported by the probe, being moved. The separated specimen is subjected to analysis through TEM, SEM, SIMS, etc.

14 Claims, 7 Drawing Sheets

METHOD FOR SEPARATING SPECIMEN AND METHOD FOR ANALYZING THE SPECIMEN SEPARATED BY THE SPECIMEN SEPARATING METHOD

BACKGROUND OF THE INVENTION

The present invention relates to a method for separating a specimen and a method for analyzing the separated specimen, and particularly relates to a method for separating a minute region from the substrate of a specimen such as a semiconductor wafer, and an analysis method using the separating method.

As a conventional technique of such a separating method, there has been a technique disclosed in "Microscopy of Semiconducting Materials Conference, Oxford, (1989), pp. 501-506". In this document, there is a description about an example in which a thin film specimen analyzed through a transmission electron microscope (hereinafter abbreviated to "TEM") is cut out by use of a focused ion beam (hereinafter abbreviated to "FIB").

According to the contents of disclosure in the above document, a chip 71 having a length of several mm and a width of 100-500 $\mu$m is cut out from a semiconductor integrated circuit by use of a diamond wafering saw, being fixedly mounted on a copper grid 72 (standard grid of the TEM for observing the chip), as shown in FIG. 7. Then the chip 71 is processed by the FIB to be formed into a thin film specimen 73. Then the thin film specimen 73 is irradiated with an electron beam 74, being observed by use of the TEM. In FIG. 7, the reference numeral 75 represents a rectangular opening.

As another conventional technique, there has been a technique disclosed in "Proceedings of International Reliability Physics Symposium, (1989), pp. 43-52". In this document, there is a description about an example in which a section of a device is processed by use of the FIB, and the structure of the section is observed by means of a function of a scanning ion microscope (hereinafter abbreviated to "SIM").

In conventional TEM observation, generally, a specimen is thinned by polishing, being observed. Therefore, it was impossible to set the place of observation and direction of the specimen desirably and precisely. Indeed the first-mentioned technique is a superior method in which an image of a specified portion of a specimen can be observed through the TEM. In this method, however, it is necessary to carry out a step in which a region having a length of several mm and a width of 100-500 $\mu$m and including a portion to be analyzed is mechanically separated from the chip of an integrated circuit or semiconductor wafer. When a wafer is a specimen substrate, it is necessary to divide the wafer for observation. Further, it is difficult to process a specimen to have a thickness not thicker than 100 $\mu$m through mechanical processing by means of a diamond wafering saw or the like from a point of view of processing accuracy and damage. Accordingly, there is a defect that the rest portions which could not be cut to be thin enough through mechanical processing is necessary to be processed with the FIB, and it takes a long time for the processing.

In the conventional observation of a section by use of the SEM, an observation specimen is cleaved, and the plane of cleavage thereof is observed. Accordingly, it is impossible to specify a desired portion precisely, and it is difficult to observe the section thereof. Indeed the above-mentioned conventional techniques have advantageous in that a section at a certain portion of a specimen can be observed. However, they have disadvantageous in that it is difficult to make a section perfectly or substantially flat and parallel to the specimen surface for observation, and it is impossible to observe, for example, a horizontal section of a contact hole.

SUMMARY OF THE INVENTION

It is an object of the present invention to provide a method for separating a specimen in which when a desired point within an integrated circuit chip or a semiconductor wafer is analyzed, only a portion to be analyzed can be taken out without dividing the chip or wafer, and the taken-out specimen can be analyzed from desired directions, and the total time required for analysis can be shortened.

In order to attain the above object, the specimen separating method and the specimen analyzing method according to the present invention are constructed as follows.

According to a first aspect of the present invention, the method for separating a minute portion from a specimen, comprises the steps of: irradiating a surface of the specimen with focused ion beams from at least two different directions so that the specimen is subjected to focused ion beam processing; connecting a probe with a portion of the specimen to be separated before the portion is separated from the specimen; and separating the portion from the specimen, while the separated portion of the specimen is supported by the probe, the separated portion being carried into a desired position.

In the method of separating a specimen according the first aspect of the present invention, preferably, the portion of the specimen and the probe are connected through a redeposition film of sputtering particles produced through the focused ion beam processing or through a beam induced deposition film formed by focused ion beam irradiation in a gas atmosphere.

Further preferably, the focused ion beam processing is etching supported by a reactive gas atmosphere.

Further preferably, the specimen is a semiconductor wafer and the probe is manufactured by use of a semiconductor manufacturing process.

Further preferably, the contact between the portion of the specimen and the probe is judged by a change in luminance of an image of secondary particles in the vicinity of the portion to be separated from the specimen.

According to a second aspect of the present invention, the method for separating a minute portion from a specimen, comprises the steps of: irradiating a surface of the specimen with a focused ion beam substantially perpendicularly to the surface, the focused ion beam being rectangularly scanned in the vicinity of a portion to be separated from said specimen to form a hole having a predetermined depth; tilting the surface of the specimen relative to an irradiation axis of the focused ion beam with an angle less the 90 degrees, and irradiating a side portion of the specimen forming the hole with the focused ion beam in order to form a bottom hole substantially parallel to the surface of the portion to be separated; irradiating the surface of the specimen with the focused ion beam substantially perpendicularly to the surface, and scanning the focused ion beam along a circumferential portion to be separated so as to form trenches along the circumferential portion; contacting a top portion of a probe of a manipulator with the surface of the portion to be separated; connecting the top portion of the probe to the surface of the portion to be separated; irradiating the surface of the specimen with the focused ion beam substantially perpendicularly to the surface, and scanning the focused ion beam along the circumferential portion to be separated so as to form a notched groove along the circumferential portion to separate the portion from the specimen; and moving the separated portion connected to the top portion of the probe to a predetermined position by the manipulator. Even if either one of the step of forming the trenches and the step of forming the bottom hole is carried out prior to the other, the purpose of specimen separation can be achieved.

In the method of separating a specimen according the second aspect of the present invention, preferably, the portion of the specimen and the probe are connected through a beam induced deposition film formed by focused ion beam irradiation in a gas atmosphere.

In the method of separating a specimen according the second aspect of the present invention, preferably, the probe is made of an electrically conductive material, being connected to a power supply through a high resistance. It is determined from a change of electric potential of the specimen whether the top portion of the probe is contacted with the portion to be separated or not.

According to a third aspect of the present invention, the method for separating a minute portion from the specimen and for analyzing the minute portion, comprises the steps of: irradiating a surface of the specimen with focused ion beams from at least two different directions so that the specimen is subjected to focused ion beam processing; connecting a probe with a portion of the specimen to be separated before the portion is separated from the specimen; separating the portion from the specimen, while the separated portion of the specimen is supported by the probe; and observing a sectional image of the separated portion of the specimen, by use of an observation means, in a state where the separated portion of the specimen is being supported by the probe.

According to a fourth aspect of the present invention, the method for separating a minute portion from the specimen and for analyzing the minute portion, comprises the steps of: irradiating a surface of the specimen with focused ion beams from at least two different directions so that the specimen is subjected to focused ion beam processing; connecting a probe with a portion of the specimen to be separated before the portion is separated from the specimen; separating the portion from the specimen, while the separated portion of the specimen is supported by the probe; partially thinning the portion of the specimen during or after separation of the portion from the specimen; and observing the thinned portion by use of a transmission electron microscope.

According to a fifth aspect of the present invention, the method for separating a minute portion from the specimen and for analyzing the minute portion, comprises the steps of: irradiating a surface of the specimen with focused ion beams from at least two different directions so that the specimen is subjected to focused ion beam processing; connecting a probe with a portion of the specimen to be separated before the portion is separated from the specimen; separating the portion from the specimen, while the separated portion of the specimen is supported by the probe; and obtaining component information of the separated portion of the specimen through secondary ion analysis, in a state where the separated portion of the specimen is being supported by the probe.

As has been described, in order to attain the foregoing object, according to the method for separating a specimen and the method for analyzing the specimen, the surface of the substrate of a specimen is processed by impinging the FIB to the surface of the substrate from at least two impinging directions, and the specimen to be separated is mechanically connected to an external probe in the step for separating a portion of the specimen to be analyzed. Therefore, it is possible to move the separated specimen desirably by moving the probe after the specimen is separated.

According to the present invention, since the surface of the substrate of a specimen is processed by impinging the FIB to the surface of the substrate from at least two impinging directions, the substrate and a minute specimen including a portion to be analyzed can be separated with each other mechanically. Further, since the separated specimen is mechanically connected to an external probe at the step for separating a portion of the specimen, it is possible to hold the separated specimen so as to move the specimen to a desired position by moving the probe. The separated specimen held by the probe can be moved separately from its original substrate into various analyzing apparatus. Further, the separated specimen can be processed again into a shape suitable for analysis. On the other hand, the substrate of the specimen after the separation can be used for other analytic or additional processes since the substrate of the specimen is not broken.

Further, since a specimen is separated by using the FIB, the size of the separated specimen can be made much smaller than that of the specimen separated by using a conventional mechanical separation method. Therefore, it is possible to shorten time required for processing a specimen into a thin film suitable for TEM observation.

BRIEF DESCRIPTION OF THE DRAWINGS

Other features and advantages of the present invention will be apparent from the following description taken in connection with the accompanying drawings, wherein.

DETAILED DESCRIPTION OF THE PREFERRED EMBODIMENTS

Embodiments of the present invention will be described hereinafter with reference to FIGS. 1 to 6.

Figure 3:
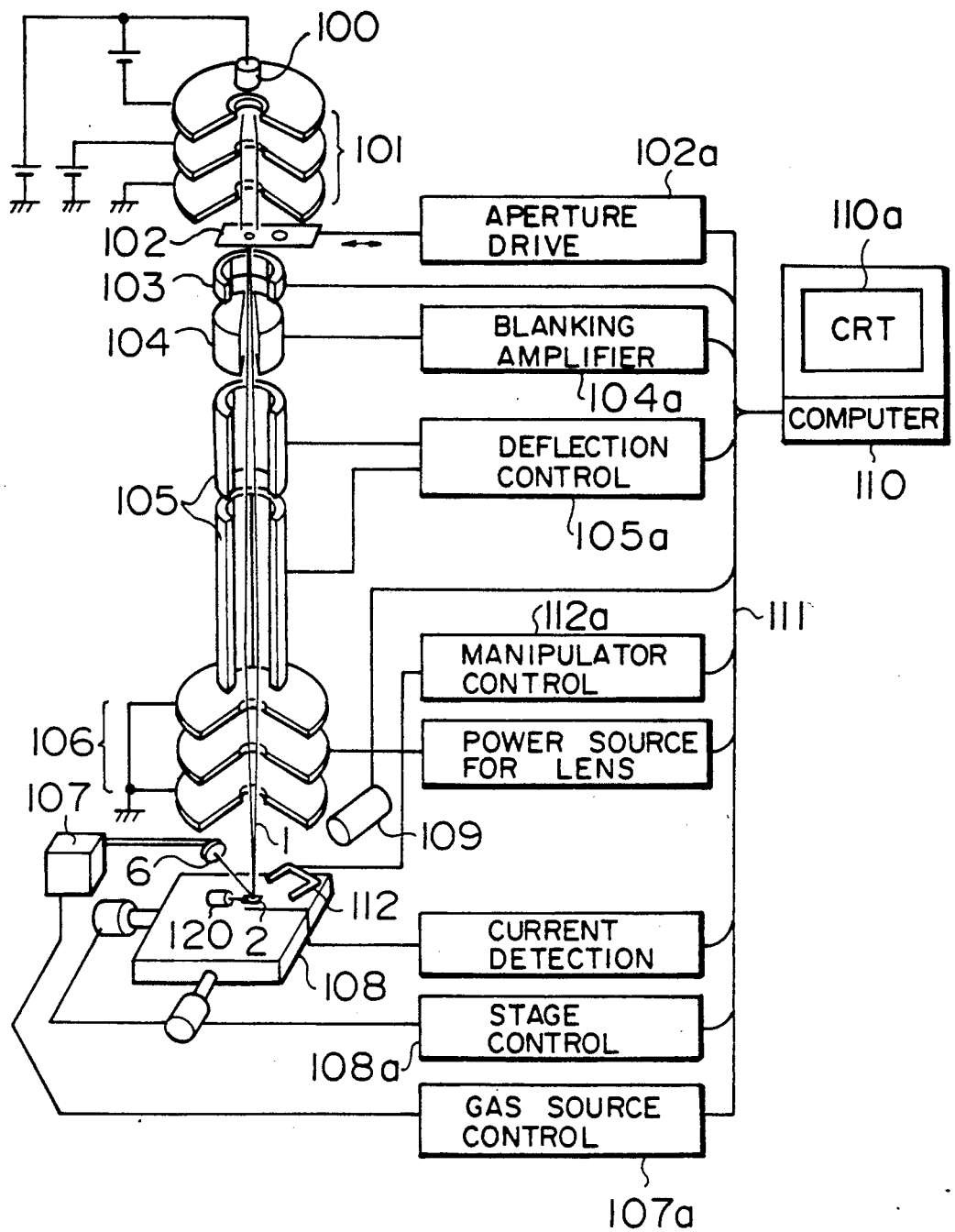
FIG. 3 is a diagram illustrating an FIB apparatus for carrying out the separation method according to the present invention.

FIG. 3 shows a fundamental construction of an FIB apparatus used in the embodiment of the present invention. Ions emitted from a liquid metal ion source 100 are made to be an FIB 1. The FIB is focused on a specimen 2 through a condenser lens 101 and an objective lens 106. A selectable aperture 102, an aligner-stigmator 103, a blanker 104 and a deflector 105 are arranged between the two lenses 101 and 106. The selectable aperture 102 is connected to an aperture driving section 102a, and the blanker 104 is connected to a blanking amplifier 104a. Further, the deflector 105 is connected to a deflection control section 105a.

On a stage 108 movable in the directions along two axes (X, Y), the specimen 2 is fixed to the rotary shaft of a specimen rotator 120 mounted on the stage 108. The stage 108 is moved by means of X-direction and Y-direction driving sections in accordance with a stage control section 108a. The rotary shaft of the specimen rotator 120 is set in parallel to the stage 108 in the FIB apparatus shown in FIG. 3.

A gas (W(CO)$_6$) produced from a gas source 107 is led to the neighborhood of a specimen irradiation section of the FIB 1 through a gas nozzle 6. The gas source 107 is controlled by a gas source control section 107a. Secondary electrons produced from the surface of the specimen 2 by irradiation with the FIB 1 are detected by a secondary electron detector 109. A secondary electron signal from the secondary electron detector 109 is converted from an analog signal into a digital signal. The digital signal is supplied to an image memory of a computer 110 in synchronism with the control of the deflection of the FIB 1, so that an image by means of a scanning ion microscope (abbreviated to "SIM") is displayed on a CRT 110a.

Figure 4:
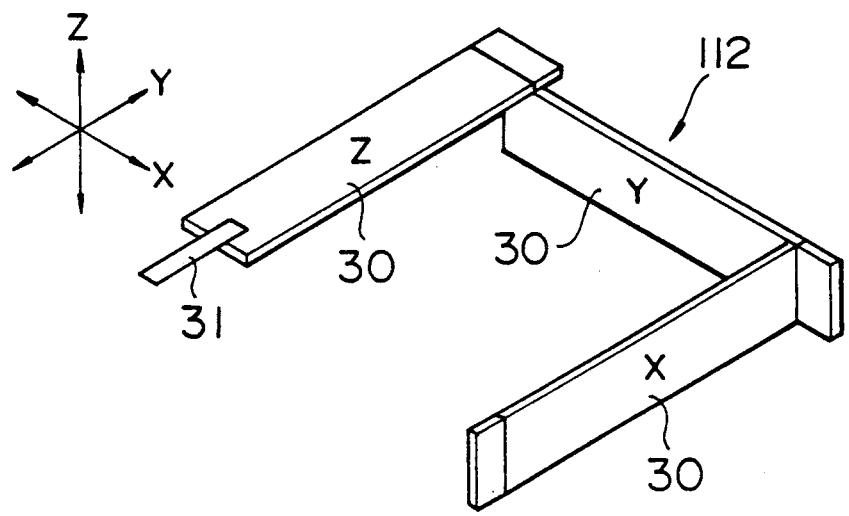
FIG. 4 is an expanded perspective view of a manipulator.

A manipulator 112 includes three bimorph type piezoelectric elements 30 connected to each other with rotation at 90° as shown in FIG. 4, so that the manipulator can be driven in three directions of axes X, Y and Z. A metal probe 31 is attached to the top end of the manipulator 112. The top end portion of the probe 31 is processed to be in the form of a plate. More specifically, the probe 31 is preferably constituted by a holder portion having a thickness not thinner than 50 μm, and a probe head having a thickness not thicker than 10 μm. The probe head is provided on one surface of the holder portion, being projected from the top end of the holder portion. The manipulator 112 is connected to a manipulator control section 112a as shown in FIG. 3.

The computer 110 controls the aperture driving section 102a through a system bus 111 to select the desired aperture from the selectable aperture 102. Further, the computer 110 controls the deflection control section 105a, the manipulator control section 112a, the stage control section 108a, the gas source control section 107a, etc., so that the computer 110 controls the beam deflecting operation of the deflector 105, the detection of the signal from the secondary electron detector 109, the driving of the manipulator 112, the displacement of the stage 108, the supply of gas, and so on.

Next, the processing on the specimen 2 by means of the FIB apparatus having the above-mentioned construction will be described hereinafter. FIG. 1 (a) to FIG. 1 (g) show an embodiment of the present invention, illustrating steps (a) through (g) for separating, from the specimen 2, a part of the specimen 2 including a portion to be analyzed. In this embodiment, the specimen 2 is a silicon substrate, and the separated part of the specimen 2 is hereinafter referred to as "a separated specimen". The process of separation will be described along the steps (a) through (g) successively.

(a) In FIG. 1 (a), the attitude of the specimen 2 is maintained so that the FIB 1 is perpendicularly radiated on the surface of the specimen 2. The FIB 1 is scanned rectangularly on the vicinity of a portion to be separated, so that a rectangular hole 3 having a required depth is formed in the surface of the specimen 2.

(b) In FIG. 1 (b) the specimen 2 is tilted so that the axis of the FIB 1 is tilted at an angle of about 70° relative to the surface of the specimen 2. The FIB 1 is radiated to a side portion of the specimen 2 in which the rectangular hole 3 is formed, so that a bottom hole 4 is formed in parallel to the surface of the portion to be separated. The tilt angle of the specimen 2 ( the attitude of the specimen 2 ) is changed by means of the specimen rotator 120.

(c) In FIG. 1 (c), the attitude of the specimen 2 is changed so that the surface of the specimen 2 is set to be perpendicular to the FIB 1 again. The FIB 1 is scanned along a circumferential portion to be separated so that trenches are formed.

(d) In FIG. 1 (d), the manipulator 112 is driven to contact the top end of the probe 31 with the portion to be separated from the specimen 2. It is judged whether the top end of the probe 31 contacts with the portion or not. The judging method will be described hereinafter.

(e) In FIG. 1 (e), the W(CO)$_6$ gas 7 is supplied from the gas nozzle 6 to the neighborhood of the portion to be separated. The FIB 1 is radiated locally onto a region of the specimen 2 including the top end of the probe 31 to form a deposition film 8. The portion to be separated from the specimen 2 and the top end of the probe 31, which are contacted with each other, are connected to each other through the deposition film 8. The portion to be separated and the probe 31 may be connected with each other by a beam induced deposition film formed by the FIB radiation in a gas atmosphere. Alternatively, the portion to be separated and the probe may be connected with each other by a redeposition film formed by sputtering particles produced by the FIB processing.

(f) In FIG. 1 (f), in order to separate the portion to be separated by using the FIB 1, the FIB 1 is scanned along the circumferential portion to be separated to elongate the trenches 5. Next, a separated specimen 9 is cut from the specimen 2. The cut-out separated specimen 9 is supported by the probe 31 connected thereto.

(g) In FIG. 1 (g), the manipulator 112 is driven to move the separated specimen 9 to a required place.

In the above embodiment, when an area to be processed by using the FIB 1 is designated, raster scanning with the FIB is previously carried out to a region including the area, and secondary electrons (typical secondary electrons) are generated from the surface of the specimen 2. The quantity of the secondary electrons is used as the luminance signal of an SIM image. The secondary electrons are detected by the secondary electron detector 109. It is easy to set the area of the specimen (in the directions along the X and Y axes) by using the SIM image. However, it is difficult to judge the contact between the probe 31 and the specimen 2 because the position information relating to the Z axis must be required to judge the contact. Namely, although rough position information relating the Z axis can be obtained from the difference of focus state of the FIB 1, it is difficult to judge the contact on the micron level.

In this embodiment, therefore, the probe 31 is made to be electrically conductive, being connected to a power source (the voltage of the power source is Vs) through a high resistance in the step (d). The electric potential of the probe 31 is substantially equal to the Vs when the probe 31 is not contacted with the specimen 2. The electric potential of the probe 31 becomes equal to the electric potential (ground potential) of the specimen 2 when the probe 31 is contacted with the specimen 2. Consequently, since the contact changes the luminance signal level of the SIM image of the probe 31, it is possible to judge the contact accurately on the basis of the change of the level.

Thereafter, the section of the cut-out separated specimen 9 is subjected to the FIB processing (finishing processing with a minute beam) again, and the section structure is observed through an SEM (scanning electron microscope). It is also possible to finish the back side of the separated specimen 9 through the same process to observe the structure thereof. Namely, according to this embodiment, it is also possible to observe a section parallel to the surface of a specimen. The separated specimen 9 held by the probe 31 may be inserted into various analyzing apparatus separately from the specimen 2 so as to be measured thereby. For example, element analysis can be performed through secondary ion mass spectroscopy (abbreviated to "SIMS"). Further, it is also possible to process the separated specimen 9 again so as to have a shape suitable for analysis. For example, after the separated specimen 9 is processed to have a wedge shape including a portion to be analyzed in its top angled portion, its components can be analyzed by a CAT method (method of composition analysis by thickness-fringe).

Figure 1A:
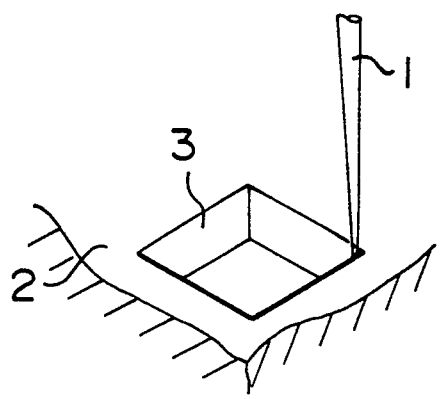
FIG. 1 (a) to FIG. 1 (g) are diagrams illustrating processes of separation in an embodiment of the separation method according to the present invention.
Figure 1B:
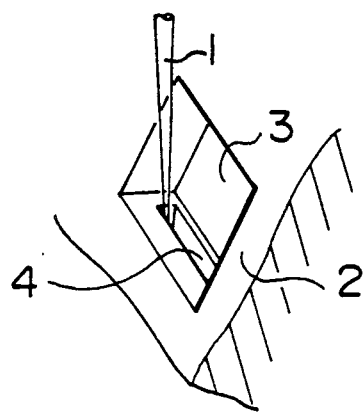
Figure 1C:
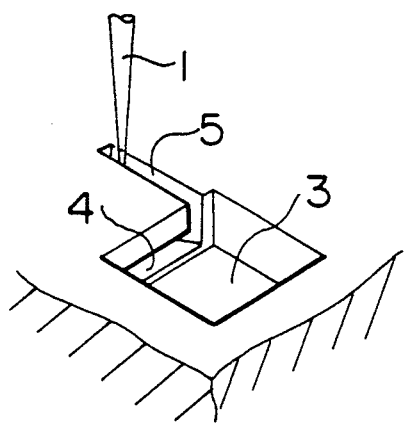
Figure 1D:
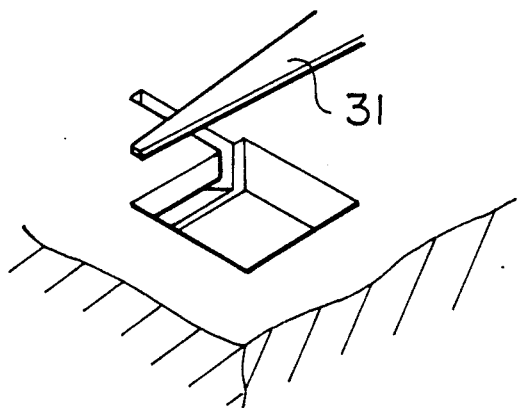
Figure 1E:
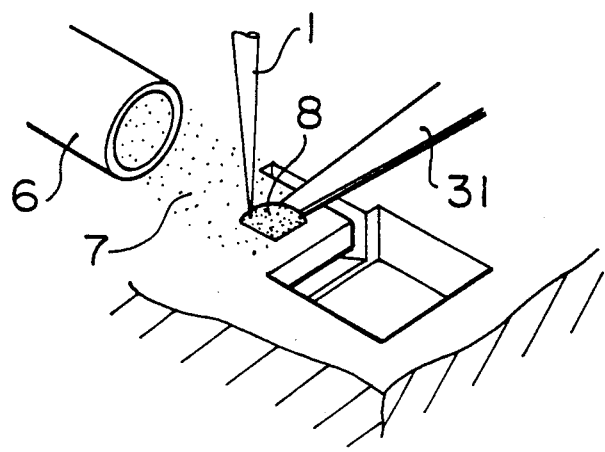
Figure 1F:
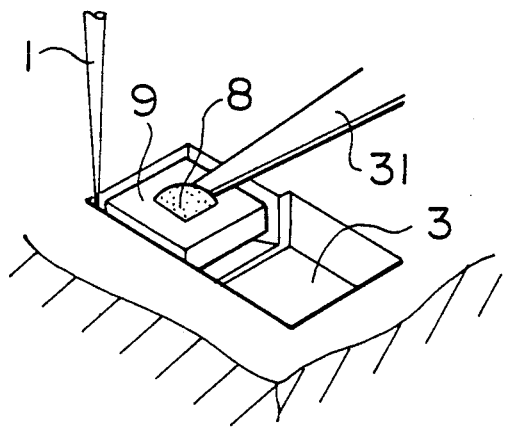
Figure 1G:
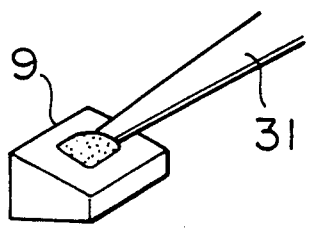
Figure 2A:
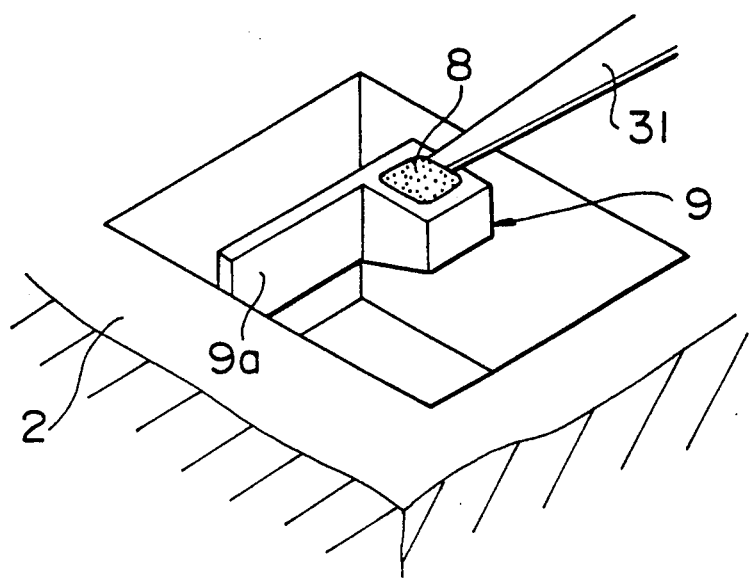
FIG. 2 (a) and FIG. 2 (b) are diagrams illustrating an example of separation process of a specimen which can be observed through a TEM.
Figure 2B:
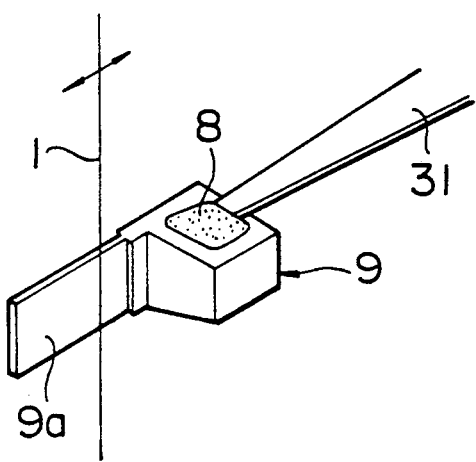

FIG. 2 (a) and FIG. 2 (b) show an embodiment in which a portion of the specimen 2 is separated in the same manner as in the above embodiment, and its separated specimen 9 is made into a thin film so as to be observed by means of a TEM.

In FIG. 2 (a), a portion 9a of the separated specimen 9 is previously cut out to be thin. In FIG. 2 (b), the thin portion 9a of the separated specimen 9 is further thinned to form a thin film by the FIB 1. The portion 9a of the separated specimen 9 is used as a specimen for the observation through a TEM. According to this embodiment, it is possible to take out a TEM specimen from a desired place of the specimen 2 easily with high accuracy, so that it is not necessary to divide the substrate of the specimen 2.

Figure 5:
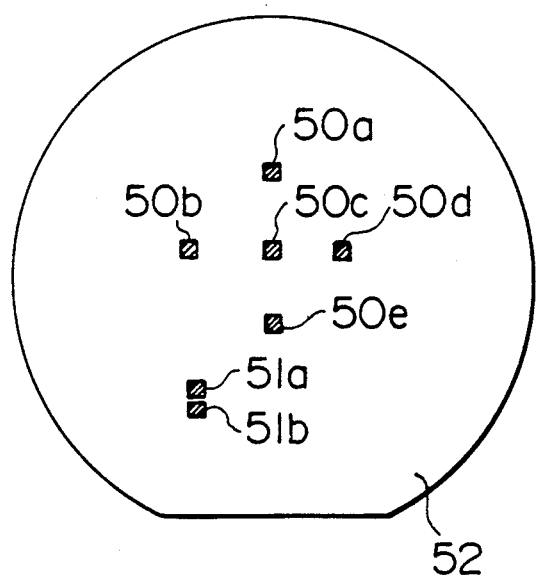
FIG. 5 is a front view of a wafer to illustrate an example of the position for cutting out a separated specimen for multi-point TEM analysis.

FIG. 5 shows an example of multi-point TEM analysis in a semiconductor wafer 52. In this example, a plurality of minute specimens in analysis points 50a to 50e, 51a, and 51b are separated from the semiconductor wafer 52, and analysis through a TEM is performed after the respective separated specimens are made to be thin films in the same manner as in the example shown in FIG. 2. A specimen stage used in the analyzing method includes a mechanism capable of moving in the X and Y directions and a mechanism capable of tilting with a wafer. According to the separating method of the invention, a number of separated specimens can be obtained from a wafer, as is apparent from the example shown in FIG. 5. In this case, a number of separated portions to be taken out give no influence to each other at the time of separating them. Therefore, it is possible to separate a plurality of specimen portions at desired places. Further, although it has been difficult to obtain two near-by specimens such as the analysis points 51a and 51b in a conventional method in which TEM specimens are obtained by dividing a wafer, it is possible to obtain two near-by specimens for TEM observation by using the separating method according to the present invention. Further, it is possible to give other analyses or additional processes to the wafer itself after a plurality of specimen portions are separated.

Although a metal member is used as a probe in the above-mentioned embodiments, a probe made of $SiO_2$, Al, W or the like produced through a semiconductor process may be used. The use of a semiconductor process has an advantage that probes of uniform shapes can be produced in great quantities at one time. If a probe is constituted by a thick holder portion and a thin and minute probe head portion, the probe is easily handled and connected to a separated specimen.

Figure 6A:
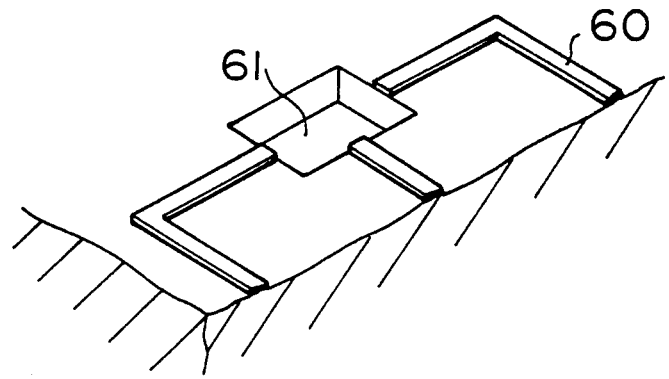
FIG. 6 (a) to FIG. 6 (c) are perspective views illustrating an example of planting of a separated specimen into another place.
Figure 6B:
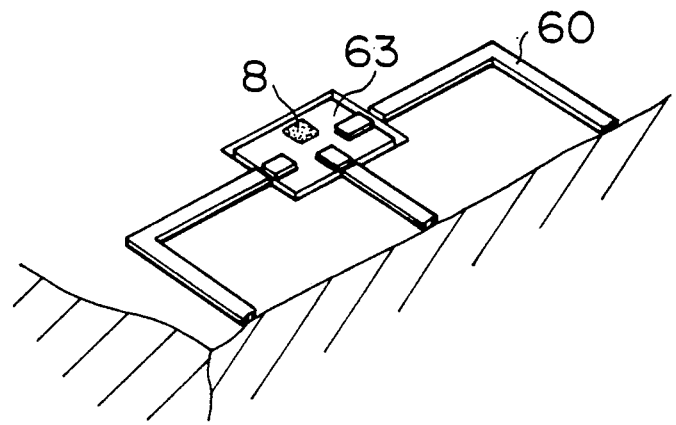
Figure 6C:
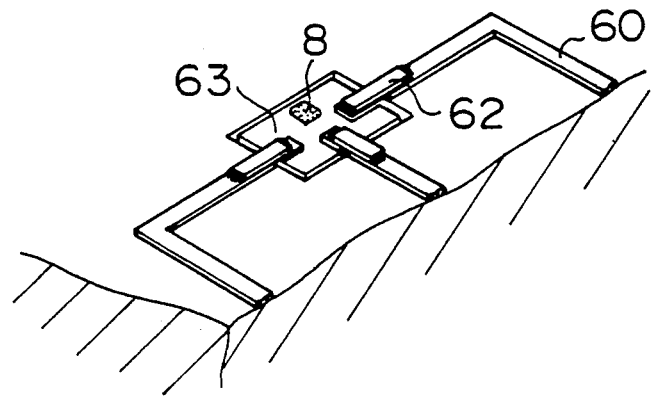
Figure 7:
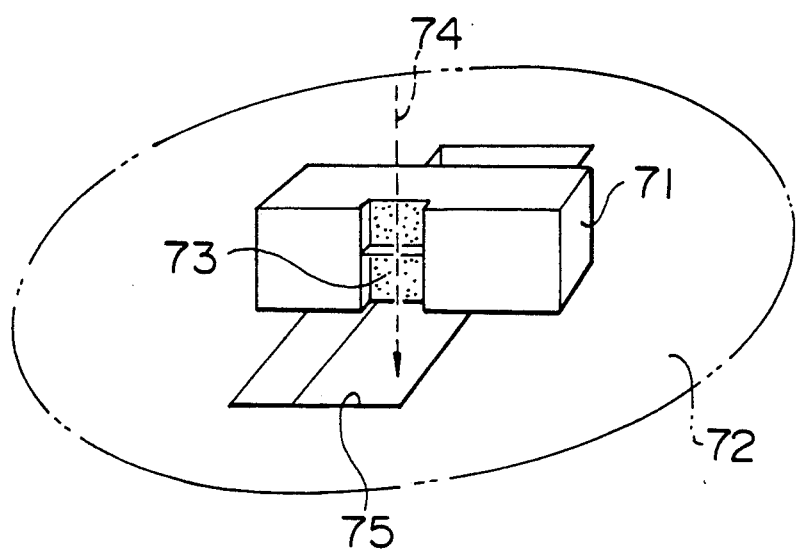
FIG. 7 is a perspective view for explaining a conventional specimen separating method and a conventional specimen analyzing method.

FIG. 6(a) to FIG. 6(c) show an embodiment in which the separation method according to the present invention is applied to a method of planting transistor elements. Transistor elements to be planted are previously separated from a chip by using the separation method according to the present invention. The process of planting will be described hereinafter.

(a) in FIG. 6 (a), a square hole 61 is formed by using an FIB in a desired portion of a substrate in which planting is to be made.

(b) in FIG. 6 (b), a manipulator is driven to carry a separated specimen 63 (for example, a transistor or the like) to the square hole 61. A probe head is cut off by using an FIB to leave the separated specimen 63 in the square hole 61.

(c) In FIG. 6 (c), an electrode on the separated specimen 63 and a wiring 60 on the chip substrate are electrically connected to each other through a plant wiring 62. The plant wiring 62 is moved by the manipulator in the same manner as the separated specimen, and the electrode and the wiring are connected with each other by means of W deposition obtained by local FIB radiation in a $W(CO)_6$ gas atmosphere.

As has been described, the separation method according to the present invention, a device formed in one chip can be easily separated from the one chip, being moved into a desired portion of another chip so as to be fused therein.

If a separated specimen has a large volume, a portion to be processed for separation by using an FIB has also a large volume. Since only a physical phenomenon of sputtering is used for the FIB processing in the above-mentioned embodiments, it takes a long time for processing. In such a case, if a reactive gas is led into the neighborhood of a portion to be processed by using the FIB, etching assisted by the FIB can improve the processing speed and processing time.

As is apparent from the above description, according to the present invention, when a desired point in a semiconductor chip or wafer is analyzed, only a required portion can be cut out by using an FIB, and the separated portion can be supported so as to be carried to a desired place. Accordingly, only a required inute region can be separated without dividing the chip or wafer substrate. Further, since the separated specimen after separation is in a state of being supported by a probe, it is possible to move the separated specimen to a desired place, and it is possible to change the attitude of the separated specimen desirably, so that analyses such as TEM observation or the like can be performed thereon. Further, since a region processed by an FIB is limited in only a circumferential portion to be analyzed, a total process volume of a substrate is so small that total time required for analysis can be shortened.

What is claimed is:

1. A method for separating a minute portion from a specimen, comprising the steps of:
   irradiating a surface of the specimen with focused ion beams from at least two different directions so that the specimen is subjected to focused ion beam processing;
   connecting a probe with a portion of said specimen to be separated before said portion is separated from said specimen; and
   separating said portion from said specimen, while said separated portion of said specimen is supported by said probe.

2. A method for separating a specimen according to claim 1, wherein said portion of said specimen and said probe are connected through a redeposition film of sputtering particles produced through the focused ion beam processing.

3. A method for separating a specimen according to claim 1, wherein said portion of said specimen and said probe are connected through a beam induced deposition film formed by focused ion beam irradiation in a gas atmosphere.

4. A method for separating a specimen according to any one of claims 1 through 3, wherein said focused ion beam processing is etching supported by a reactive gas atmosphere.

5. A method for separating a specimen according to claim 1, wherein said specimen s a semiconductor wafer.

6. A method for separating a specimen according to claim 1, wherein said probe includes a holder section having a thickness not thinner than 50 μm, and a probe head provided on one surface of said holder section, said probe head being projected from the top end of said holder section, said probe head having a thickness not thicker than 10 μm.

7. A method for separating a specimen according to claim 6, wherein said probe is manufactured by use of a semiconductor manufacturing process.

8. A method for separating a specimen according to any one of claims 1 through 3, wherein the contact between said portion of said specimen and said probe is judged by a change in luminance of an image of secondary particles in the vicinity of said portion to be separated from said specimen.

9. A specimen analysis method for separating a minute portion from the specimen and for analyzing the minute portion, comprising the steps of:
   irradiating a surface of the specimen with focused ion beams from at least two different directions so that the specimen is subjected to focused ion beam processing;
   connecting a probe with a portion of said specimen to be separated before said portion is separated from said specimen;
   separating said portion from said specimen, while said separated portion of said specimen is supported by said probe; and
   observing a sectional image of said separated portion of said specimen, by use of an observation means, in a state where said separated portion of said specimen is being supported by said probe.

10. A specimen analysis method for separating a minute portion from the specimen and for analyzing the minute portion, comprising the steps of:
    irradiating a surface of the specimen with focused ion beams from at least two different directions so that the specimen is subjected to focused ion beam processing;
    connecting a probe with a portion of said specimen to be separated before said portion is separated from said specimen;
    separating said portion from said specimen, while said separated portion of said specimen is supported by said probe;
    partially thinning said portion of said specimen during or after separation of said portion from said specimen; and
    observing said thinned portion by use of a transmission electron microscope.

11. A specimen analysis method for separating a minute portion from the specimen and for analyzing the minute portion, comprising the steps of:
    irradiating a surface of the specimen with focused ion beams from at least two different directions so that the specimen is subjected to focused ion beam processing;
    connecting a probe with a portion of said specimen to be separated before said portion is separated from said specimen;
    separating said portion from said specimen, while said separated portion of said specimen is supported by said probe; and
    obtaining component information of said separated portion of said specimen through secondary ion analysis, in a state where said separated portion of said specimen is being supported by said probe.

12. A method for separating a minute portion from a specimen, comprising the steps of:
    irradiating a surface of the specimen with a focused ion beam substantially perpendicularly to said surface, said focused ion beam being rectangularly scanned in the vicinity of a portion to be separated from said specimen to form a hole having a predetermined depth;
    tilting said surface of the specimen relative to an irradiation axis of said focused ion beam with an angle less the 90 degrees, and irradiation a side portion of said specimen forming said hole with the focused ion beam in order to form a bottom hole substantially parallel to the surface of said portion to be separated;
    irradiation said surface of the specimen with said focused ion beam substantially perpendicularly to said surface, and scanning said focused ion beam along a circumferential portion to be separated so as to form trenches along said circumferential portion;
    contacting a top portion of a probe of a manipulator with the surface of said portion to be separated;
    connecting said top portion of said probe to the surface of said portion to be separated;
    irradiating said surface of said specimen with said focused ion beam substantially perpendicularly to said surface, and scanning said focused ion beam along said circumferential portion to be separated so as to form a notched groove along said circumferential portion to separate said portion from said specimen; and moving said separated portion connected to said top portion of said probe to a predetermined position by said manipulator.

13. A method for separating a specimen according to claim 12, wherein said portion of said specimen and said top portion of said probe are connected through a beam induced deposition film formed by the focused ion beam irradiation in a gas atmosphere.

14. A method for separating a specimen according to claim 12, wherein said probe is made of an electrically conductive material, being connected to a power supply through a high resistance, and wherein it is determined from a change of electric potential of said specimen whether said top portion of said probe is contacted with said portion to be separated or not.

* * * * *